United States Patent
Sasai et al.

(10) Patent No.: US 12,402,861 B2
(45) Date of Patent: Sep. 2, 2025

(54) MEDICAL SYSTEM AND CONTROL METHOD FOR MEDICAL SYSTEM

(71) Applicant: OLYMPUS CORPORATION, Tokyo (JP)

(72) Inventors: Ryota Sasai, Tokyo (JP); Toshiyuki Mori, Mitaka (JP); Takeaki Ishizawa, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 405 days.

(21) Appl. No.: 17/939,135

(22) Filed: Sep. 7, 2022

(65) Prior Publication Data
US 2023/0026537 A1    Jan. 26, 2023

Related U.S. Application Data

(63) Continuation of application No. PCT/JP2020/010473, filed on Mar. 11, 2020.

(51) Int. Cl.
*A61B 8/00*    (2006.01)
*G01S 7/52*    (2006.01)

(52) U.S. Cl.
CPC .............. *A61B 8/5207* (2013.01); *A61B 8/46* (2013.01); *G01S 7/52053* (2013.01)

(58) Field of Classification Search
CPC ......... A61B 8/5207; A61B 8/46; A61B 8/085; A61B 8/08; A61B 8/12; G01S 7/52053
See application file for complete search history.

(56) References Cited

U.S. PATENT DOCUMENTS

2007/0167814 A1* 7/2007 Wakabayashi ....... A61B 8/4494
600/459
2008/0194999 A1* 8/2008 Yamaha ......... A61B 17/320068
601/2
(Continued)

FOREIGN PATENT DOCUMENTS

JP    2000-237205 A    9/2000
JP    2004229823 A     8/2004
(Continued)

OTHER PUBLICATIONS

International Search Report dated May 12, 2020 issued in PCT/JP2020/010473.
(Continued)

*Primary Examiner* — Santiago Garcia
(74) *Attorney, Agent, or Firm* — Scully, Scott, Murphy & Presser, P.C.

(57) ABSTRACT

A medical system includes: an endoscope; an ultrasonic probe; and a control device that is connected to the endoscope and the ultrasonic probe, generates a display image from a captured image acquired by the endoscope, and generates an echo image from an ultrasonic wave acquired by the ultrasonic probe, wherein the control device acquires a first echo image in which a target tissue is displayed on a central axis, acquires a second echo image obtained by scanning a cross section different from the first echo image at a reference position of the ultrasonic probe from which the first echo image was acquired, and compares a central axis of the second echo image with a position of the target tissue in the second echo image.

17 Claims, 14 Drawing Sheets

(56) References Cited

U.S. PATENT DOCUMENTS

| | | | |
|---|---|---|---|
| 2009/0118621 A1* | 5/2009 | Harhen | A61B 8/445 |
| | | | 600/466 |
| 2019/0151036 A1* | 5/2019 | Steger | A61B 90/361 |
| 2019/0159759 A1* | 5/2019 | Murakami | A61B 8/12 |
| 2020/0167912 A1* | 5/2020 | Xu | G06V 10/26 |
| 2021/0219943 A1* | 7/2021 | Jeon | A61B 8/5223 |

FOREIGN PATENT DOCUMENTS

| | | |
|---|---|---|
| JP | 2007136133 A | 6/2007 |
| JP | 2015144623 A | 8/2015 |
| JP | 2019093123 A | 6/2019 |

OTHER PUBLICATIONS

Japanese Office Action dated Dec. 5, 2023 received in 2022-507068.

\* cited by examiner

MEDICAL SYSTEM AND CONTROL METHOD FOR MEDICAL SYSTEM

CROSS-REFERENCE TO RELATED APPLICATIONS

This application is a continuation application based on a PCT Patent Application No. PCT/JP2020/010473, filed on Mar. 11, 2020, the entire content of which is hereby incorporated by reference.

BACKGROUND

Technical Field

The present invention relates to a medical system including an ultrasonic probe.

Background Art

Conventionally, in laparoscopic surgery, a method of performing treatment by inserting a treatment tool or an endoscope through separate holes (openings) opened in the abdominal wall has been used. Laparoscopic surgery uses a smaller incision and is less invasive than open surgery.

In surgery to remove a target tissue such as a tumor under laparoscopic surgery, a surgeon needs to accurately grasp the position of the target tissue in the organ to be treated before starting the excision of the target tissue. To do this, the surgeon uses an ultrasonic probe to obtain an echo image of the organ and estimate the location of the target tissue in the organ. The surgeon acquires an echo image by controlling the position and orientation of the distal end of the ultrasonic probe based on the image captured by the laparoscope. Since it is difficult to accurately recognize the position and orientation of the distal end of the ultrasonic probe from the display screen of the laparoscope, even if the target tissue is displayed on the echo image, it is difficult to estimate the exact position of the target tissue in the organ. Therefore, the surgeon obtains a plurality of echo images of the organ by appropriately changing the position and orientation of the distal end of the ultrasonic probe, and comprehensively evaluates them to estimate the position of the target tissue in the organ.

Japanese Patent Application No. 2004-229823 (hereinafter referred to as Patent Document 1) describes an ultrasonic diagnostic apparatus that provides orientation control support to the user when the user operates the ultrasonic probe to control the position and orientation of the distal end of the ultrasonic probe. The ultrasonic diagnostic apparatus described in Patent Document 1 assists in controlling the position and orientation of the ultrasonic probe by using the change in the cross-sectional shape of the luminal tissue due to the change in the orientation of the ultrasonic probe when diagnosing the lumen tissue. The ultrasonic diagnostic apparatus assists in controlling the position and orientation of the ultrasonic probe so that the scanning plane of the ultrasonic beam becomes orthogonal to the central axis of the blood vessel more quickly and accurately.

The ultrasonic diagnostic apparatus described in Patent Document 1 can be used for diagnosing a luminal tissue whose cross-sectional shape changes due to a change in the orientation of an ultrasonic probe. The ultrasonic diagnostic apparatus can determine whether the scanning surface of the ultrasonic beam for the central axis direction of the blood vessel is appropriate, but cannot determine whether the scanning surface of the ultrasonic beam for the organ is appropriate. That is, the ultrasonic diagnostic apparatus described in Patent Document 1 cannot streamline the work for estimating the accurate position of the target tissue in the organ.

SUMMARY

The present invention provides a medical system that streamlines the work for estimating the exact position of a target tissue in an organ.

A medical system includes: an endoscope; an ultrasonic probe; and a control device that is connected to the endoscope and the ultrasonic probe, generates a display image from a captured image acquired by the endoscope, and generates an echo image from an ultrasonic wave acquired by the ultrasonic probe, wherein the control device acquires a first echo image in which a target tissue is displayed on a central axis, acquires a second echo image obtained by scanning a cross section different from the first echo image at a reference position of the ultrasonic probe from which the first echo image was acquired, and compares a central axis of the second echo image with a position of the target tissue in the second echo image.

The medical system of the present invention can streamline the work for estimating the accurate position of the target tissue in the organ.

DETAILED DESCRIPTION OF THE PREFERRED EMBODIMENTS

First Embodiment

The first embodiment of the present invention will be described with reference to FIGS. 1 to 11.

Figure 1:
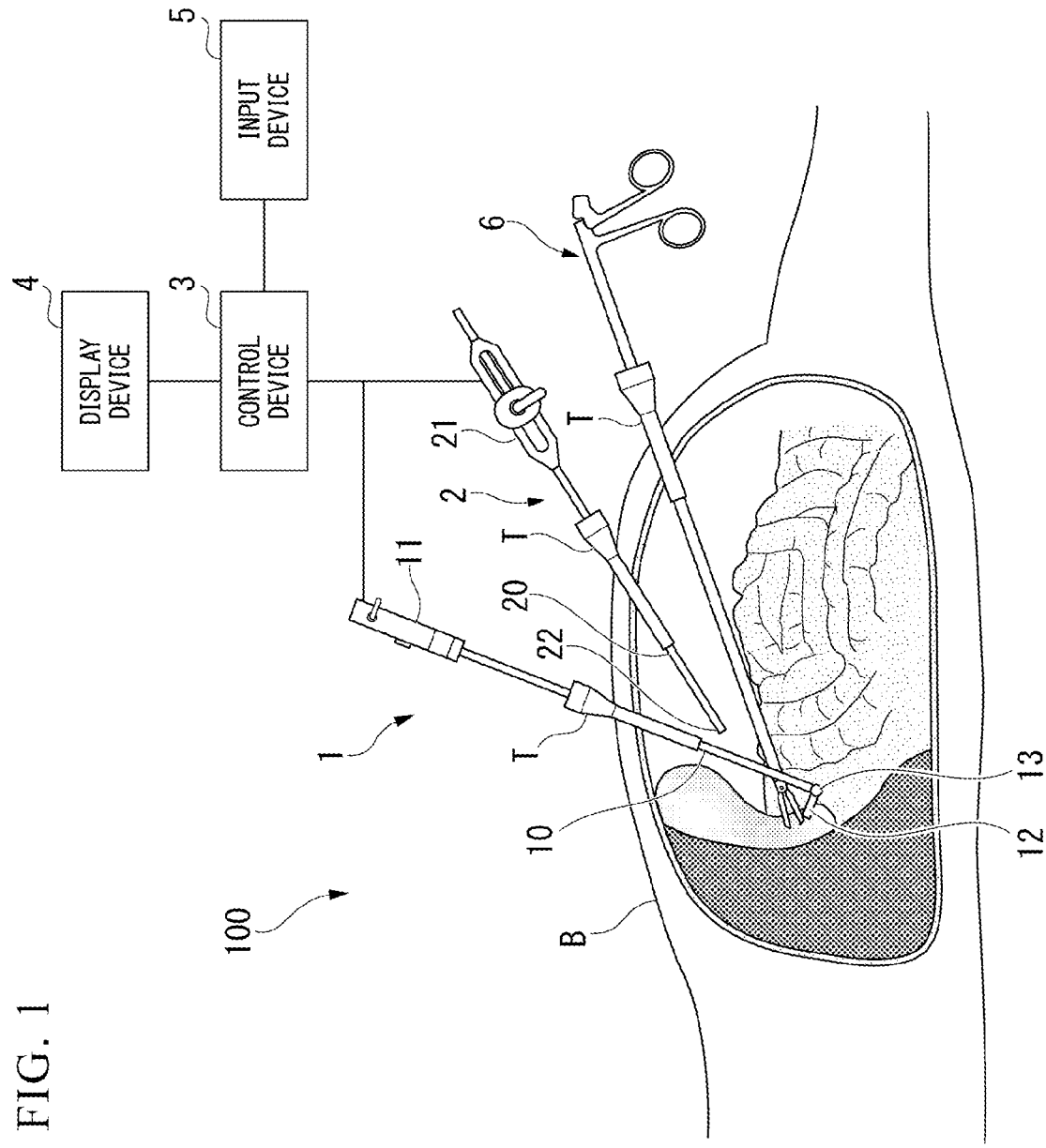
FIG. 1 is a diagram showing an overall configuration of a medical system according to a first embodiment of the present invention.

FIG. 1 is a diagram showing the overall configuration of a medical system 100 according to the present embodiment.

[Medical System 100]

As shown in FIG. 1, the medical system 100 includes an ultrasonic probe 1, an endoscope 2, a control device 3, a display device 4, and an input device 5. The medical system 100 is a system that supports a procedure in which the ultrasonic probe 1 or the endoscope 2 is inserted through separate holes (openings) opened in the abdominal wall in laparoscopic surgery. The medical system 100 may further include grasping forceps 6 to assist processing with the ultrasonic probe 1.

The ultrasonic probe 1 includes an insertion portion 10, an operation portion 11 provided on the proximal end side of the insertion portion 10, a treatment portion 12 provided on the distal end side of the insertion portion 10, and a curved portion 13 provided between the insertion portion 10 and the treatment portions 12. The treatment portion 12 is attached to the insertion portion 10 via the curved portion 13 that can be curved. The surgeon can operate the curved portion 13 to change the orientation of the treatment portion 12 with respect to the insertion portion 10. The insertion portion 10 and the treatment portion 12 are formed in a long shape that can be inserted into the abdominal cavity (inside the body cavity) of the patient from a trocar T. The surgeon passes the treatment portion 12 and the insertion portion 10 through the trocar T punctured in the abdomen B of the patient, and introduces the treatment portion 12 and the insertion portion 10 into the abdominal cavity.

The operation portion 11 is a member operated by the surgeon. The surgeon can change the position and orientation of the treatment portion 12 of the ultrasonic probe 1 by moving the ultrasonic probe 1 by holding the operation portion 11.

The treatment portion 12 generates ultrasonic waves and receives ultrasonic waves reflected from the living body. The treatment portion 12 has a mechanism appropriately selected from known ultrasonic probe mechanisms. For example, the treatment portion 12 has a piezoelectric element (oscillator) that generates ultrasonic waves, an acoustic lens, and the like. The treatment portion 12 scans by a linear method, a convex scan method, a phased method, or the like, and the cross section scanned by the treatment portion 12 is a cross section parallel to the longitudinal axis of the treatment portion 12. In a case where the treatment portion 12 performs a convex scan, the cross section scanned by the treatment portion 12 is a cross section (fan shape) parallel to the longitudinal axis of the treatment portion 12.

Inside the insertion portion 10 and the operation portion 11, a control signal line for controlling the treatment portion 12, a power line for supplying electric power to the treatment portion 12, and the like are wired. The control signal line, power line, and the like are connected to the control device 3.

The endoscope (imaging device) 2 has a long and rigid insertion portion 20 that can be inserted into the abdominal cavity of the patient, and a handle portion 21. The surgeon passes the insertion portion 20 through the trocar T punctured in the abdomen B of the patient and introduces the insertion portion 20 into the abdominal cavity.

The insertion portion 20 has an imaging portion 22 at the distal end thereof.

The imaging portion 22 has a lens and an imaging element for photographing the inside of the abdomen of the patient. In the insertion portion 20 introduced into the abdominal cavity, the imaging portion 22 is arranged at a position in the abdomen where the affected portion to be treated can be photographed. The imaging portion 22 may have an optical zoom or an electronic zoom function.

The handle portion 21 is a member operated by the surgeon. The surgeon can change the position and orientation of the imaging portion 22 of the endoscope 2 by moving the endoscope 2 by holding the handle portion 21. The insertion portion 20 may further have a curved portion. By bending the curved portion provided in a part of the insertion portion 20, the position and orientation of the imaging portion 22 can be changed.

Inside the handle portion 21, a control signal line for controlling the imaging portion 22, a transmission signal for transferring the captured image captured by the imaging portion 22, and the like are wired. The control signal line, the transmission signal, and the like are connected to the control device 3.

The control device 3 receives the captured image captured by the imaging portion 22 of the endoscope 2 and transfers it to the display device 4 as a display image. Further, the control device 3 controls the treatment portion 12 of the ultrasonic probe 1.

The control device 3 is a program-executable device (computer) including a processor such as a CPU (Central Processing Unit) and hardware such as a memory. The function of the control device 3 can be realized as a function of the program (software) by reading and executing the program for controlling the processor by the control device 3. In addition, at least a part of the control device 3 may be configured by a dedicated logic circuit or the like. Further, the same function can be realized by connecting at least a part of the hardware constituting the control device 3 with a communication line.

Figure 2:
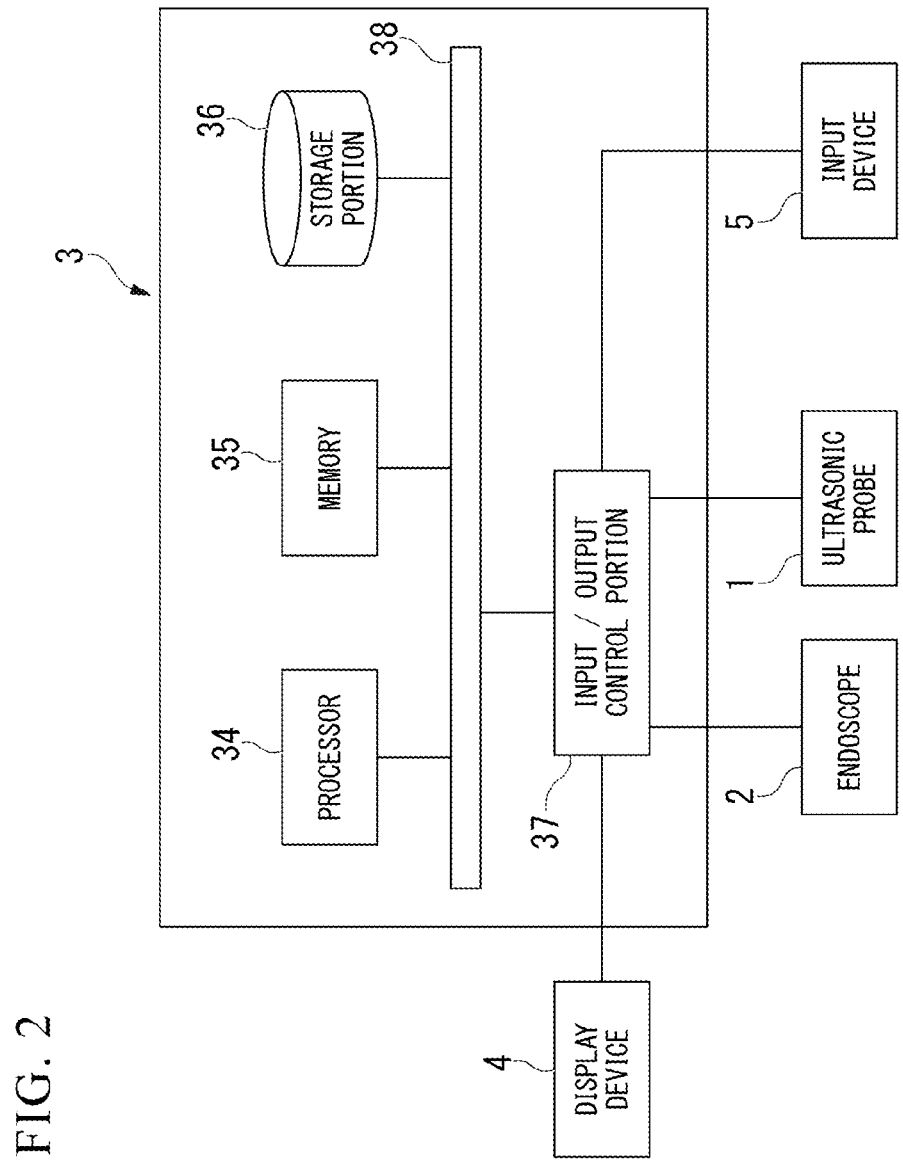
FIG. 2 is a block diagram of a control device of the medical system.

FIG. 2 is a block diagram of the control device 3.

The control device 3 has a processor 34, a memory 35 capable of reading a program, a storage portion 36, an input/output control portion 37, and a data bus 38. The processor 34, the memory 35, the storage portion 36, and the input/output control portion 37 input/output data via the data bus 38. A program that controls the operation of the control device 3 is read into the memory 35 and executed by the processor 34.

The storage portion 36 is a non-volatile recording medium that stores the above-mentioned program and necessary data. The storage portion 36 is composed of, for example, a ROM, a hard disk, or the like. The program recorded in the storage portion 36 is read into the memory 35 and executed by the processor 34.

The input/output control portion 37 receives the input data from the endoscope 2 and transfers the input data to the processor 34 or the like. Further, the input/output control portion 37 generates data, a control signal, and the like for the ultrasonic probe 1, the endoscope 2, and the display device 4 based on the instruction of the processor 34.

The control device 3 receives the captured image as input data from the endoscope 2 and reads the captured image into the memory 35. Based on the program read into the memory 35, the processor 34 performs image processing on the captured image. The captured image subjected to the image processing is transferred to the display device 4 as the display image D1.

The control device 3 performs image processing such as image format conversion, contrast adjustment, and resizing processing on the captured image to generate the display image D1. Further, the control device 3 performs image processing for superimposing a virtual image such as a tumor TU, which will be described later, on the display image D1.

The control device 3 controls the treatment portion 12 of the ultrasonic probe 1. The control device 3 causes the treatment portion 12 of the ultrasonic probe 1 to transmit and receive ultrasonic waves. Further, the control device 3 generates an echo image D2 of a living body based on the received ultrasonic waves.

Here, the control device 3 is not limited to the device provided in one piece of hardware. For example, the control device 3 may be configured by separating the processor 34, the memory 35, the storage portion 36, and the input/output control portion 37 as separate hardware, and connecting the hardware to each other via a communication line. Alternatively, the control device 3 may be implemented as a cloud system by separating the storage portion 36 and connecting it with a communication line.

The control device 3 may further include elements necessary for controlling the operation of the control device 3 other than the processor 34, the memory 35, the storage portion 36, and the input/output control portion 37 shown in FIG. 2. For example, the control device 3 may further have an image calculation portion that performs some or all of the image processing and the image recognition processing performed by the processor 34. By further having an image calculation portion, the control device 3 can execute specific image processing and image recognition processing at high speed. Further, the control device 3 may further have an image transfer portion that transfers the display image D1 and the echo image D2 from the memory 35 to the display device 4.

The display device 4 is a device that displays the display image D1 and the echo image D2 transferred by the control device 3. The display device 4 is a known monitor such as an LCD display. The display device 4 may have a plurality of monitors. The display device 4 may include a head-mounted display or a projector instead of the monitor.

The display device 4 can also display a GUI (Graphical User Interface) image generated by the control device 3 as a GUI. For example, the display device 4 can display the control information display and the surgery support display of the medical system 100 to the surgeon by GUI. Further, in a case where the control device 3 requires information input from the surgeon, the display device 4 can also display a message prompting the input device 5 to input information and a GUI display necessary for information input.

The input device 5 is a device in which the surgeon inputs an instruction or the like to the control device 3. The input device 5 is, for example, a keyboard or a mouse. Further, the input device 5 may be configured by a switch or may be configured by a touch panel integrated with the display device 4. The input to the input device 5 is transmitted to the control device 3.

Further, the input device 5 is a device for inputting an instruction to the treatment portion 12 of the ultrasonic probe 1. The input device 5 has, for example, an operation button, and the operation button is a button for inputting an operation instruction to the ultrasonic probe 1.

[Operation of the Medical System 100]

Next, the operation of the medical system 100 will be described with reference to FIGS. 3 to 12 by taking laparoscopic surgery as an example. In the present embodiment, the treatment target is liver L tissue.

First, the surgeon provides a plurality of holes (openings) for installing the trocar T in the abdomen of the patient, and punctures the trocar T in the holes.

Next, a scopist operates the endoscope 2 to pass the insertion portion 20 of the endoscope 2 through the trocar T punctured in the abdomen of the patient, and introduces the insertion portion 20 into the abdominal cavity. The endoscope 2 is fixed by a known endoscope holder or the like. Next, the surgeon passes the insertion portion 10 of the ultrasonic probe 1 through the trocar T punctured in the abdomen of the patient, and introduces the insertion portion 10 into the abdominal cavity. In addition, the surgeon also introduces the grasping forceps 6 into the abdominal cavity in the same manner as necessary.

Figure 3:
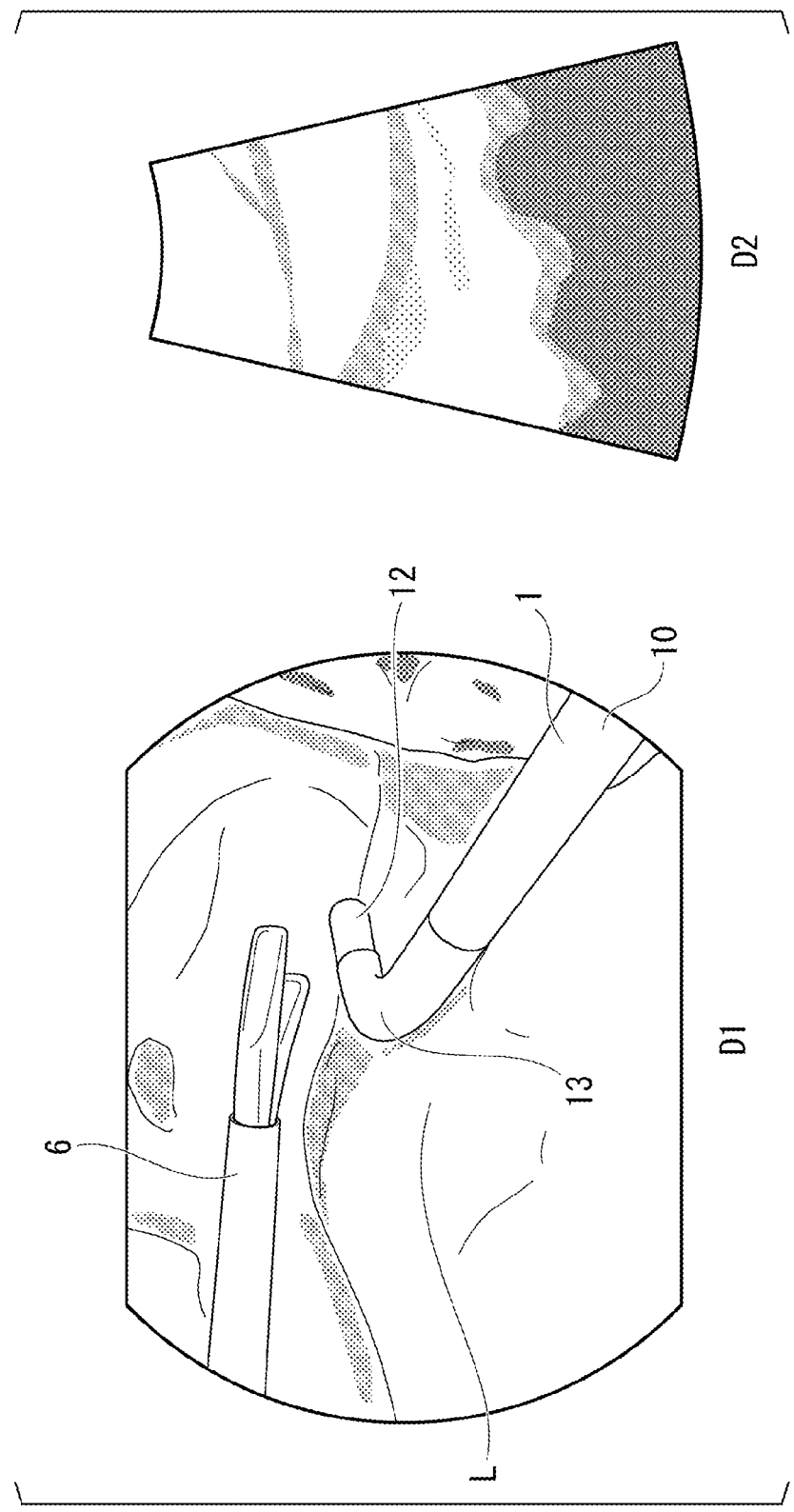
FIG. 3 is a diagram showing a display image and an echo image displayed on the display device of the medical system.

FIG. 3 is a diagram showing a display image D1 and an echo image D2 displayed on the display device 4.

While observing the display image D1, the surgeon operates the ultrasonic probe 1 so that the target tissue TU of the liver L to be treated is displayed on the central axis O of the echo image D2 displayed on the display device 4. It is desirable to operate the ultrasonic probe 1 so that the center of the target tissue TU is displayed in the center of the echo image D2. The target tissue TU is a tumor, a blood vessel, or the like.

Figure 4:
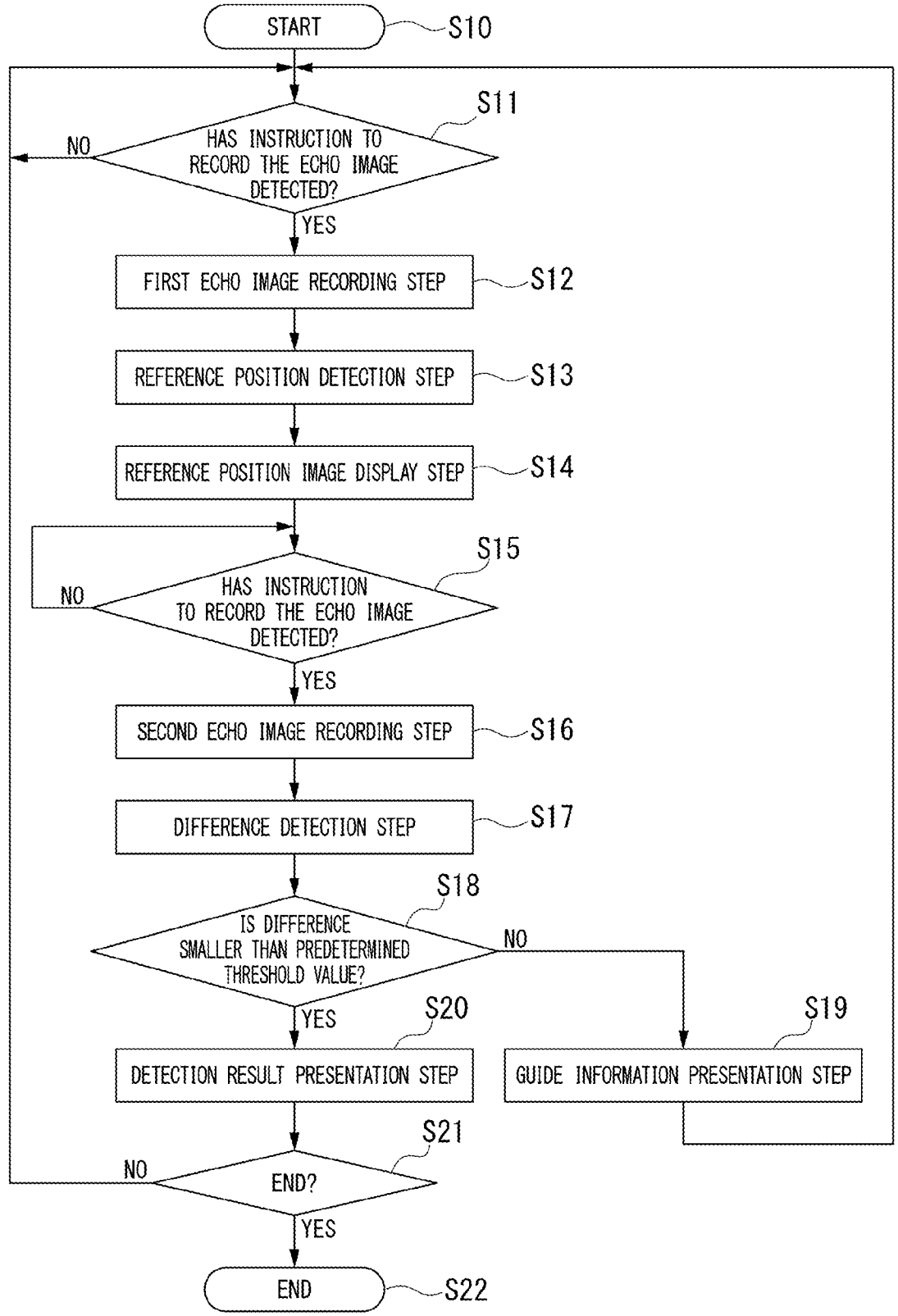
FIG. 4 is a control flowchart of the control device.

Hereinafter, an explanation will be given according to the control flowchart of the control device 3 shown in FIG. 4. As shown in FIG. 4, when the control device 3 is activated, the control device 3 starts control after performing initialization (step S10). Next, the control device 3 executes step S11.

In step S11, the control device 3 detects an instruction to record the echo image D2. The control device 3 waits until it detects an instruction to record the echo image D2 from the input device 5. When the control device 3 detects the instruction to record the echo image D2, the control device 3 executes step S12.

In step S12, the control device 3 records the echo image D2 generated based on the ultrasonic waves received from the ultrasonic probe 1 (first echo image-recording step). The echo image D2 in which the recorded target tissue TU of the liver L is reflected on the central axis O is referred to as the first echo image SE. It is desirable to record the echo image D2 in which the center of the target tissue TU is reflected in the center. Next, the control device 3 executes step S13.

In step S13, the control device 3 detects the reference position P, which is the position of the treatment portion 12 of the ultrasonic probe 1 when the first echo image SE is recorded (reference position detection step). The position of the treatment portion 12 to be detected is the center of the treatment portion 12 in the longitudinal axis direction. The control device 3 detects the two-dimensional coordinates of the reference position P in the two-dimensional coordinate system (two-dimensional display coordinate system C1) of the display image D1. For the detection of the two-dimensional coordinates of the reference position P, a method appropriately selected from known position detection methods and the like is used. For example, the two-dimensional coordinates of the reference position P may be detected by a known template-matching method.

The control device 3 may detect the three-dimensional coordinates of the reference position P in the three-dimensional coordinate system (three-dimensional display coordinate system C2) of the display space displayed by the display image D1. For the detection of the three-dimensional coordinates of the reference position P, a method appropriately selected from known position detection methods and the like is used. For example, a sensor for detecting the insertion angle and the insertion amount is attached to the trocar T, and the reference position P may be detected based on the position of the distal end of the endoscope 2 or the treatment portion 12 of the ultrasonic probe 1 detected by the sensor. Further, a position sensor is attached near the treatment portion 12 of the ultrasonic probe 1 and the distal end of the endoscope 2, and the position of the treatment point P may be detected based on the relative position between the treatment portion 12 detected by the sensor and the distal end of the endoscope 2. Further, the control device 3 may detect the reference position P by detecting the position of the treatment portion 12 in the display image D1 by image processing.

The detected reference position P is recorded in the storage portion 36. Next, the control device 3 executes step S15.

Figure 5:
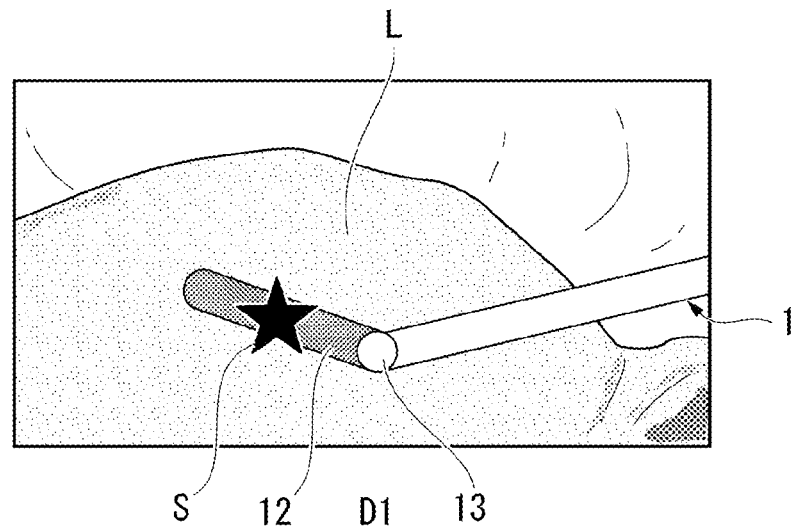
FIG. 5 is a diagram showing a display image in which a reference position image is superimposed and displayed.

FIG. 5 is a diagram showing a display image D1 in which the reference position image S is superimposed and displayed.

In step S14, the control device 3 superimposes and displays the reference position image S on the detected reference position P with respect to the display image D1. In a case where the detected reference position P is a position in the three-dimensional display coordinate system C2, the control device 3 superimposes and displays the reference position image S on the position in the two-dimensional display coordinate system C1 in which the reference position P is projected onto the display image D1. In the present embodiment, the reference position image S is a star-shaped image, but the reference position image S is not limited to this.

Figure 6:
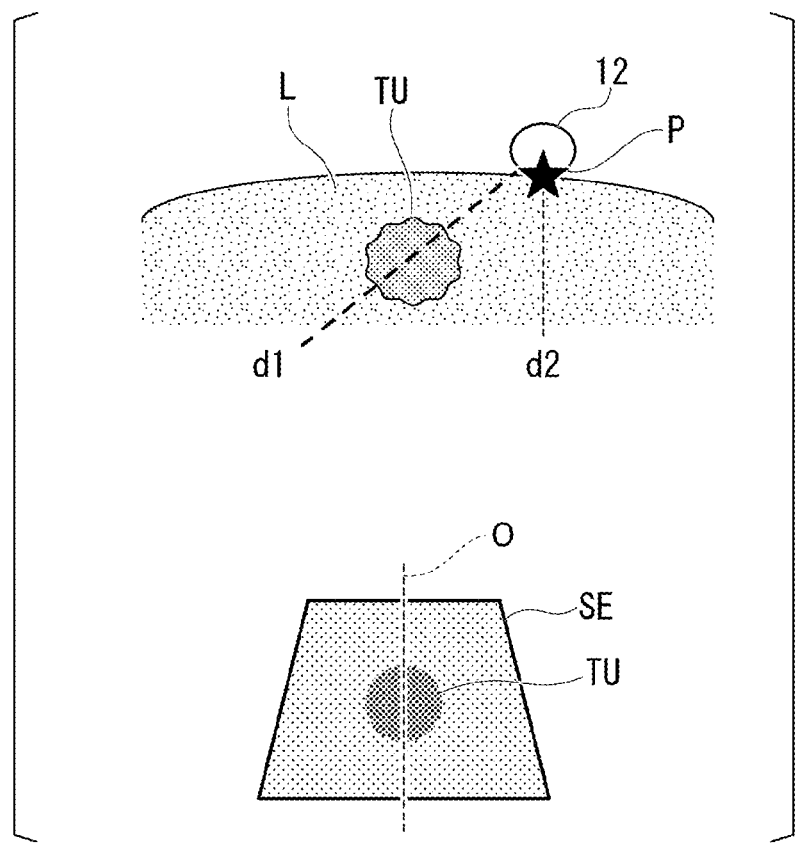
FIG. 6 is a diagram showing an example of the relationship between a reference position and a reference echo image.

FIG. 6 is a diagram showing an example of the relationship between the reference position P and the first echo image SE.

The target tissue TU is shown in the first echo image SE, but the relative position of the target tissue TU with respect to the reference position P is unknown at the time of step S14. For example, as shown in FIG. 6, the observation direction d1 of the treatment portion 12 of the ultrasonic probe 1 may not coincide with the normal direction d2 of the surface of the liver L at the reference position P.

Figure 7:
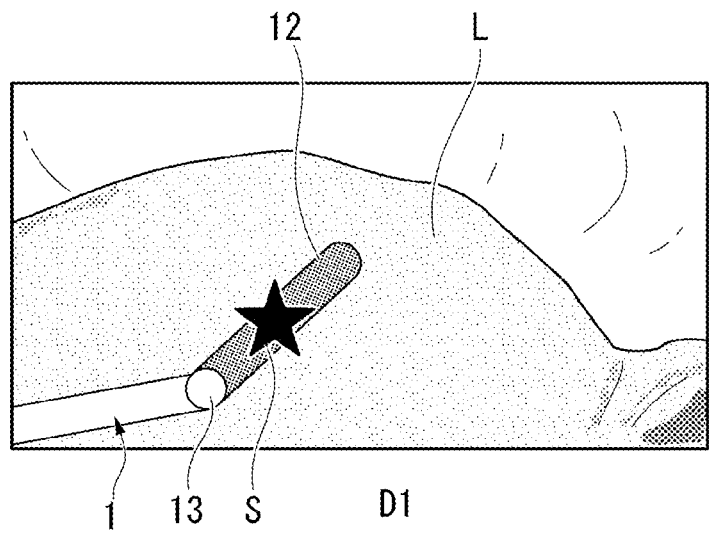
FIG. 7 is a diagram showing a display image when the position of the treatment portion of the ultrasonic probe is changed.

FIG. 7 is a diagram showing a display image D1 when the position of the treatment portion 12 is changed.

The surgeon rotates the treatment portion 12 of the ultrasonic probe 1 around the reference position image S displayed on the display image D1. Specifically, by changing the direction of the insertion portion 10 around the trocar while curving the curved portion 13 of the ultrasonic probe 1, or pulling out the insertion portion 10 from the trolley into which the insertion portion 10 is inserted and inserting it into another trocar, the surgeon rotates the treatment portion 12 in the longitudinal axis direction at the reference position P. The surgeon rotates the treatment portion 12 while generally maintaining the state in which the treatment portion 12 is arranged on the tangent plane between the treatment portion 12 and the surface of the liver L. The tangent plane is a plane perpendicular to the normal direction d2 of the surface of the liver L. In the example shown in FIG. 7, the treatment portion 12 of the ultrasonic probe 1 is rotated by about 90 degrees with respect to the reference position image S, but the rotation angle is not limited to this.

In step S15, the control device 3 detects an instruction to record the echo image D2. The control device 3 waits until it detects an instruction to record the echo image D2 from the input device 5. When the control device 3 detects the instruction to record the echo image D2, the control device 3 executes step S16.

In step S16, the control device 3 stores the echo image D2 generated based on the ultrasonic waves received from the ultrasonic probe 1 (second echo image-recording step). The second echo image acquired after performing the rotation operation of the treatment portion 12 described above is an echo image obtained by scanning a cross section different from the first echo image at the reference position P. That is, the longitudinal axis direction of the treatment portion 12 when the first echo image is acquired and the longitudinal axis direction of the treatment portion 12 when the second echo image is acquired are different. The saved echo image D2 is referred to as a second echo image AE. Next, the control device 3 executes step S17.

Figure 8:
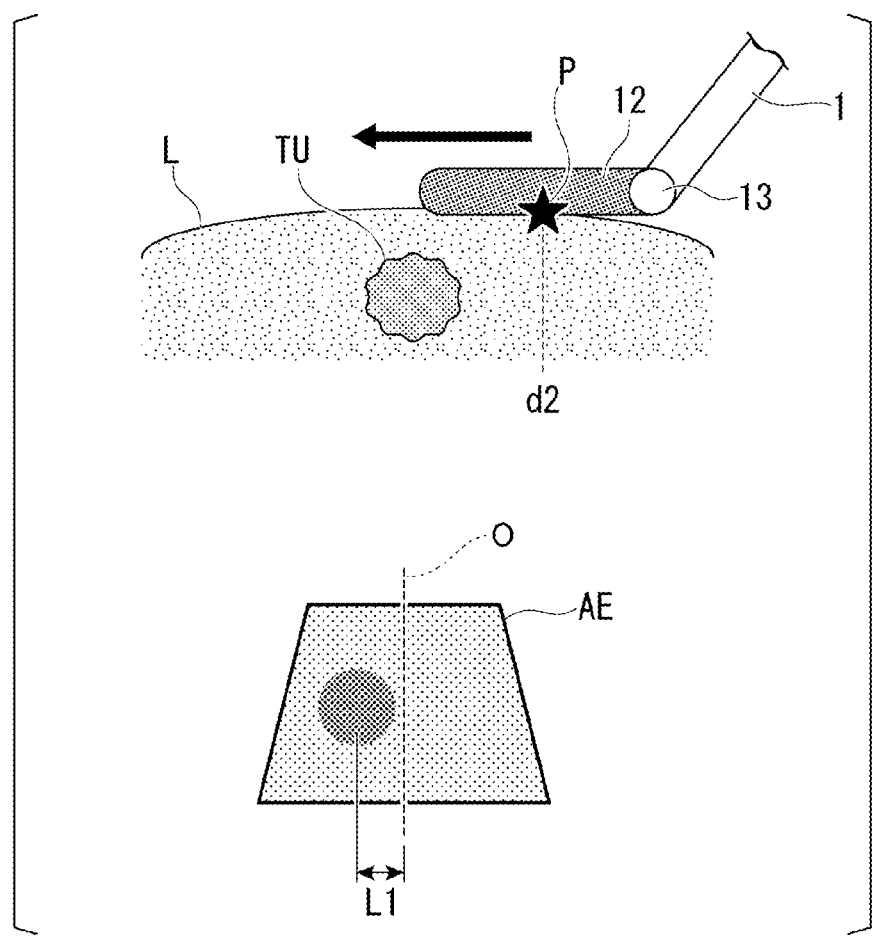
FIG. 8 is a diagram showing an example of the relationship between a reference position and an auxiliary echo image.
Figure 9:
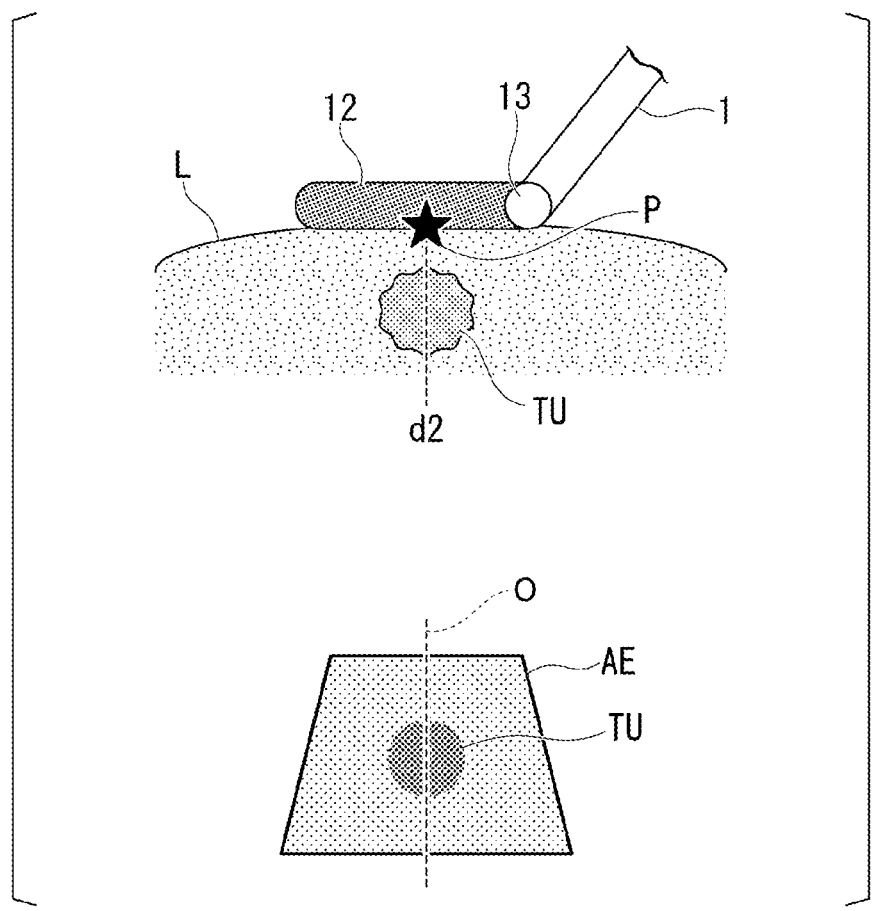
FIG. 9 is a diagram showing an example of the relationship between a reference position and an auxiliary echo image.

FIGS. 8 and 9 are diagrams showing an example of the relationship between the reference position P and the second echo image AE.

In step S17, the control device 3 compares the position of the central axis O of the second echo image AE with the position of the target tissue TU, and detects the difference (positional deviation) in the position of the target tissue TU with respect to the central axis O (difference detection step). The difference in position is the difference in position between the central axis O and the target tissue TU in the horizontal direction perpendicular to the central axis O on the second echo image. The central axis O is the central axis of the second echo image AE and is an axis along the depth direction (ultrasonic beam direction) of the ultrasonic wave from the treatment portion 12. The position of the target tissue TU is, for example, the central position of the target tissue TU. For example, as shown in FIG. 8, in the second echo image AE, the target tissue TU is located at a position separated by L1 from the central axis O, and the difference in position is L1. On the other hand, as shown in FIG. 9, in the second echo image AE, the target tissue TU is on the central axis O. Next, the control device 3 executes step S18.

In step S18, the control device 3 compares the difference in position detected in step S17 with a predetermined threshold value. In a case where the difference in the position of the target tissue TU with respect to the central axis O is smaller than a predetermined threshold value, it can be determined that the target tissue TU is located in the normal direction d2 of the surface of the liver L at the reference position P. On the other hand, in a case where the difference in the position of the target tissue TU with respect to the central axis O is equal to or greater than a predetermined threshold value, it can be determined that there is no target tissue TU in the normal direction d2 of the surface of the liver L at the reference position P. For example, as shown in FIG. 8, in the second echo image AE, the target tissue TU is located at a position separated by L1 from the central axis O. L1 is equal to or higher than a predetermined threshold value. In this case, as shown in FIG. 8, it can be determined that there is no target tissue TU in the normal direction d2 of the surface of the liver L at the reference position P. On the other hand, as shown in FIG. 9, when the target tissue TU is on the central axis O in the second echo image AE, it can be determined that the target tissue TU is in the normal direction d2 of the surface of the liver L at the reference position P. In a case where the difference between the positions detected in step S17 is equal to or greater than a predetermined threshold value, the control device 3 executes step S19. In a case where the difference between the positions detected in step S17 is smaller than the predetermined threshold value, the control device 3 executes step S20.

Figure 10:
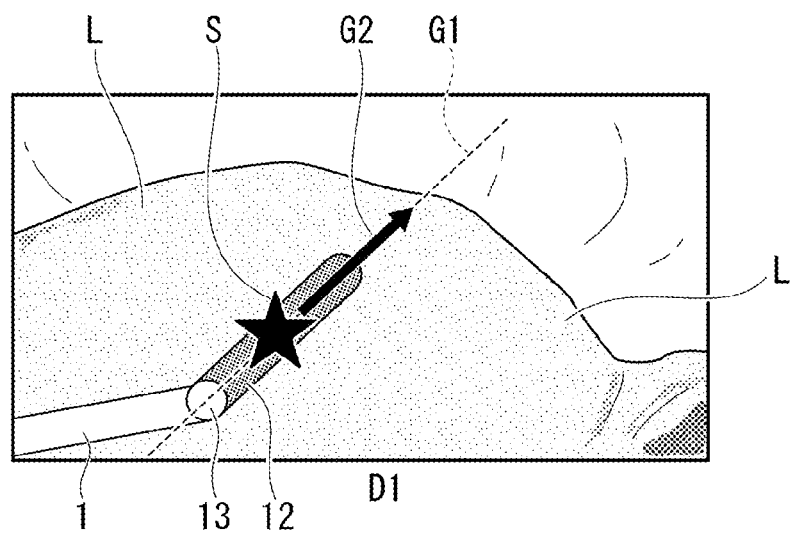
FIG. 10 is a diagram showing a display image in which support information is presented.

In step S19, the control device 3 presents guide information to the surgeon based on the determination result of step S18 (guide information presentation step). FIG. 10 is a diagram showing a display image D1 in which guide information is presented. For example, as shown in FIG. 10, the control device 3 superimposes and displays the guide line G1 and the guide arrow G2 on the display image D1, which supports moving of the treatment portion 12 to a position where the difference in position disappears and the target tissue TU is determined to be in the normal direction d2 on the surface of the liver L. As shown in FIG. 8, the control device 3 calculates the guide line G1 and the guide arrow G2 from the position of the target tissue TU away from the central axis O in the second echo image AE, and superimposes and displays the guide line G1 and the guide arrow G2 on the display image D1. For example, the control device 3 calculates the direction of the guide line G1 from the longitudinal axis direction of the treatment portion 12 on the display screen D1, and calculates the length of the guide arrow from the amount of deviation of the target image TU of the second echo image AE from the central axis O.

The surgeon refers to the guide information and moves the treatment portion 12 of the ultrasonic probe 1 around the reference position image S again. Next, the control device 3 executes step S11 again. The control device 3 records a new first echo image and a second echo image by using the treatment portion 12 moved to a new position. These steps are repeated until the difference between the positions detected in step S18 becomes smaller than a predetermined threshold value.

Figure 11:
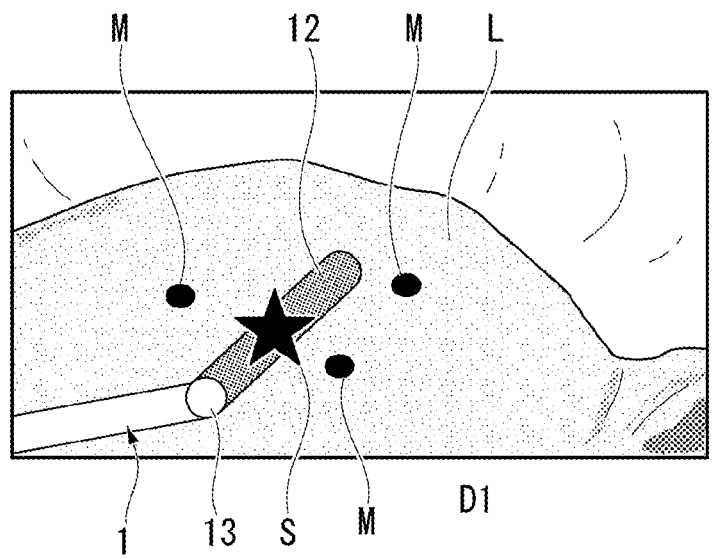
FIG. 11 is a diagram showing a display image in which measurement points are displayed.

FIG. 11 is a diagram showing a display image D1 in which the measurement point M is displayed.

In step S20, the control device 3 presents the detection result of step S18. The control device 3 may present support information in addition to the detection result. For example, as shown in FIG. 11, the control device 3 sets a plurality of measurement points M around the reference position P. The control device 3 calculates the surface shape of the liver L with reference to the measurement point M based on a known method. The control device 3 calculates the position of the target tissue TU in the three-dimensional display coordinate system C2 based on the surface shape of the liver L and the position of the target tissue TU in the auxiliary echo image AE shown in FIG. 9.

Figure 12:
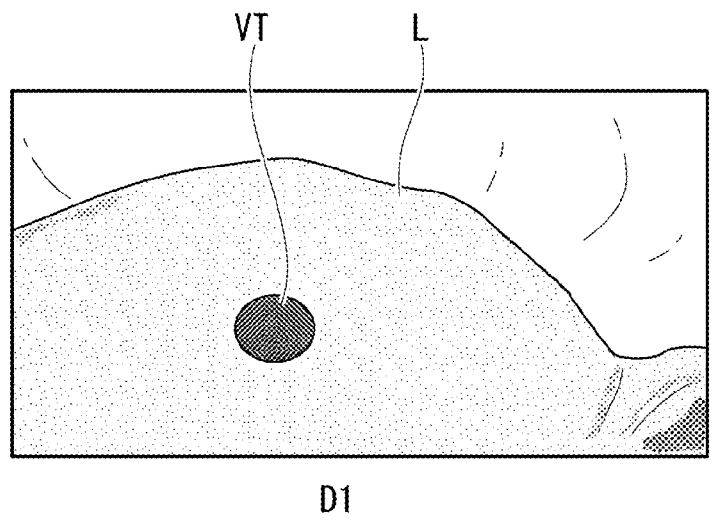
FIG. 12 is a diagram showing a display image in which a virtual image of a tumor is displayed.

FIG. 12 is a diagram showing a display image D1 in which a virtual image VT of the target organization TU is displayed.

The control device 3 superimposes and displays the virtual image VT of the target organization TU on the display image D1 at the position in the three-dimensional display coordinate system C2 of the target organization TU. The surgeon can accurately excise the liver L while checking the virtual image VT of the target tissue TU, for example.

The control device 3 then executes step S21. In step S21, it is determined whether the control device 3 ends the control. In a case where the control is not terminated, the control device 3 executes step S11 again. In a case where the control is terminated, the control device 3 then performs step S22 to end the control.

In a case where the surgeon does not use the reference position image S and does not need to display the reference position image S on the display image D1, step S13 (reference position detection step) and step S14 (reference position image display step) may not be performed. It is easier for the surgeon to rotate the treatment portion 12 when the reference position image S is displayed on the display image D1. In particular, in a case where the curved portion 13 of the ultrasonic probe 1 is curved or the ultrasonic probe 1 is inserted from another trocar, it is easier for the surgeon to rotate the treatment portion 12 when the reference position image S is displayed on the display image D1.

The control device 3 may perform step S20 without performing step S18 after detecting the difference in position in step S17. The control device 3 may display the detection result regardless of whether or not the difference between the positions detected in step S17 is equal to or greater than a predetermined threshold value.

According to the medical system 100 of the present embodiment, the first echo image can be acquired from the second echo image AE so that the target tissue TU is reflected in the center, and it is possible to detect the difference in the position of the target tissue TU with respect to the central axis O of the second echo image AE acquired at the reference position P from which the first echo image was acquired. This can support the determination of whether or not the target tissue TU is present in the normal direction d2 of the surface of the liver L at the reference position P. Therefore, it is possible to streamline the work for estimating the accurate position of the target tissue TU in the liver L. Further, the medical system 100 can display the guide line G1 and the guide arrow G2 on the display image D1, which guides the treatment portion 12 to be moved to a position where it is determined that the target tissue TU is located in the normal direction d2 on the surface of the liver L when the difference in position disappears. Further, the medical system 100 can superimpose and display the virtual image VT of the target organization TU on the display image D1.

Although the first embodiment of the present invention has been described in detail with reference to the drawings, the specific configuration is not limited to this embodiment and includes design changes and the like within a range not deviating from the gist of the present invention. In addition, the components shown in the above-described embodiment and the modifications shown below can be appropriately combined and configured.

(Modification 1)

For example, in the above embodiment, the support information is the guide line G1 and the guide arrow G2, but the support information is not limited to this. The support information may be, for example, voice information.

Second Embodiment

The second embodiment of the present invention will be described with reference to FIGS. 13 to 17. In the following description, the same reference numerals will be given to the configurations common to those already described, and duplicate description will be omitted.

A medical system 100B includes an ultrasonic probe 1, an endoscope 2, a control device 3, a display device 4, and an input device 5, as in the medical system 100 according to the first embodiment. The medical system 100B differs from the medical system 100 according to the first embodiment only in the control performed by the control device 3. Hereinafter, a description will be given according to the control flowchart of the control device 3 shown in FIG. 13.

As in the first embodiment, the surgeon operates the ultrasonic probe 1 so that the target tissue TU of the liver L to be treated is displayed on the echo image D2 displayed on the display device 4 while observing the display image D1. In the second embodiment, the target tissue TU may not be displayed on the central axis O of the echo image D2.

Figure 13:
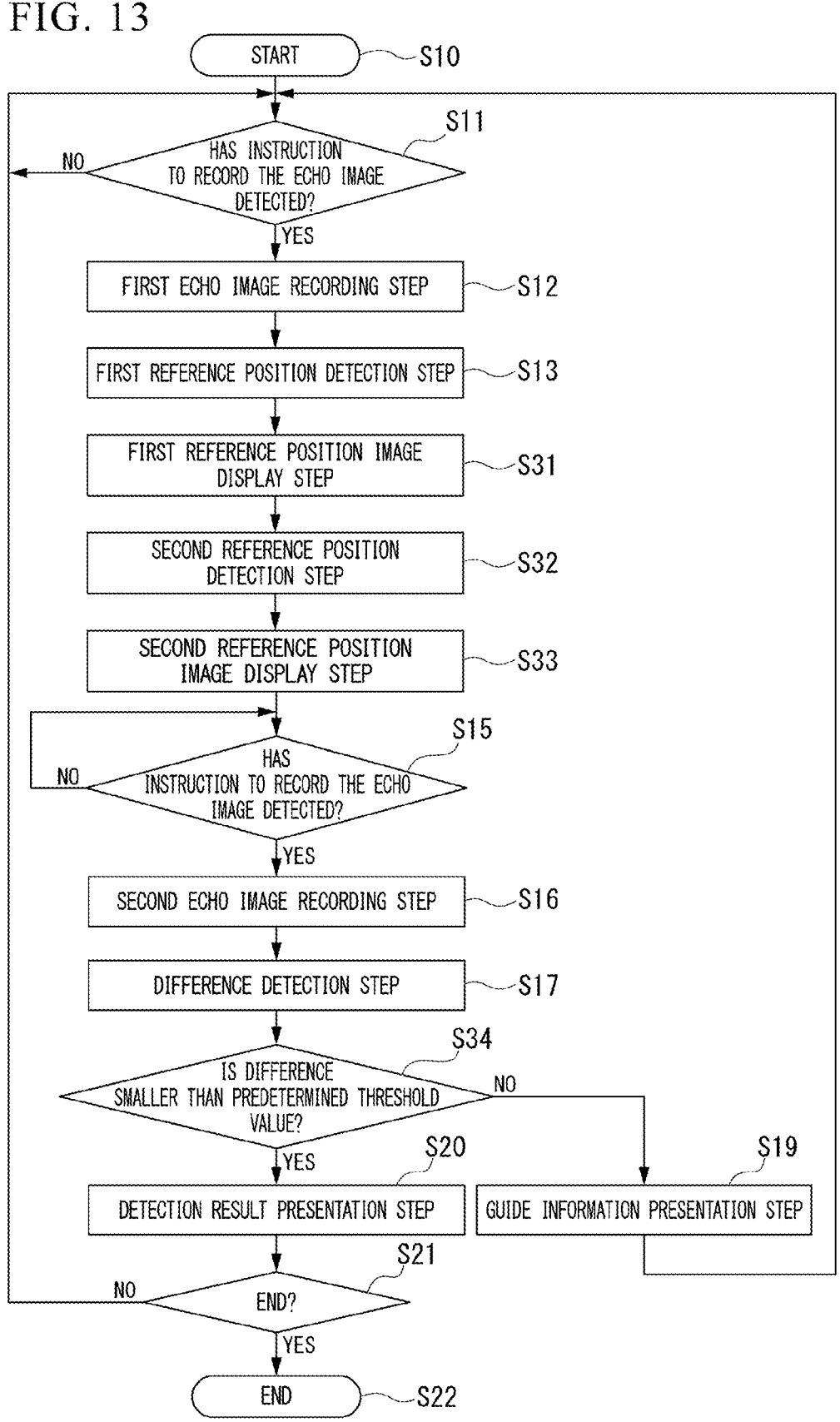
FIG. 13 is a control flowchart of a medical system according to a second embodiment of the present invention.

As shown in FIG. 13, when the control device 3 is activated, the control device 3 starts control after performing initialization (step S10). Next, the control device 3 executes step S11. Steps S11 to S13 are the same as those in the first embodiment. The control device 3 records the first echo image SE and detects the first reference position P. Next, the control device 3 executes step S31.

In step S31, the control device 3 superimposes and displays the first reference position image S on the detected first reference position P with respect to the center in the longitudinal axis direction of a treatment portion 12 of the display image D1 (first reference position image display step). Then, when the treatment portion 12 is moved in the display image D1, the control device 3 also displays the first reference position image S in a follow-up manner. Specifically, the control device 3 always displays the first reference position image S in the center in the longitudinal axis direction of the treatment portion 12 in accordance with the movement of the treatment portion 12. In the present embodiment, the first reference position image S is a star-shaped image, but the first reference position image S is not limited to this.

Figure 14:
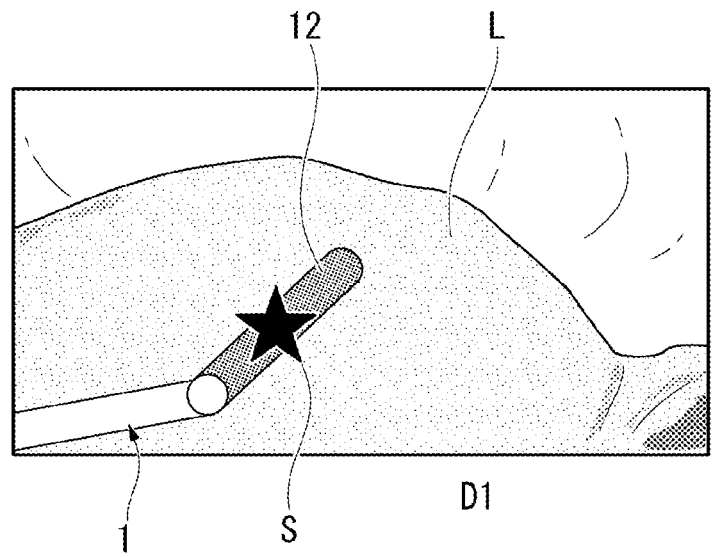
FIG. 14 is a diagram showing a display image in which a first reference position image is superimposed and displayed.
Figure 15:
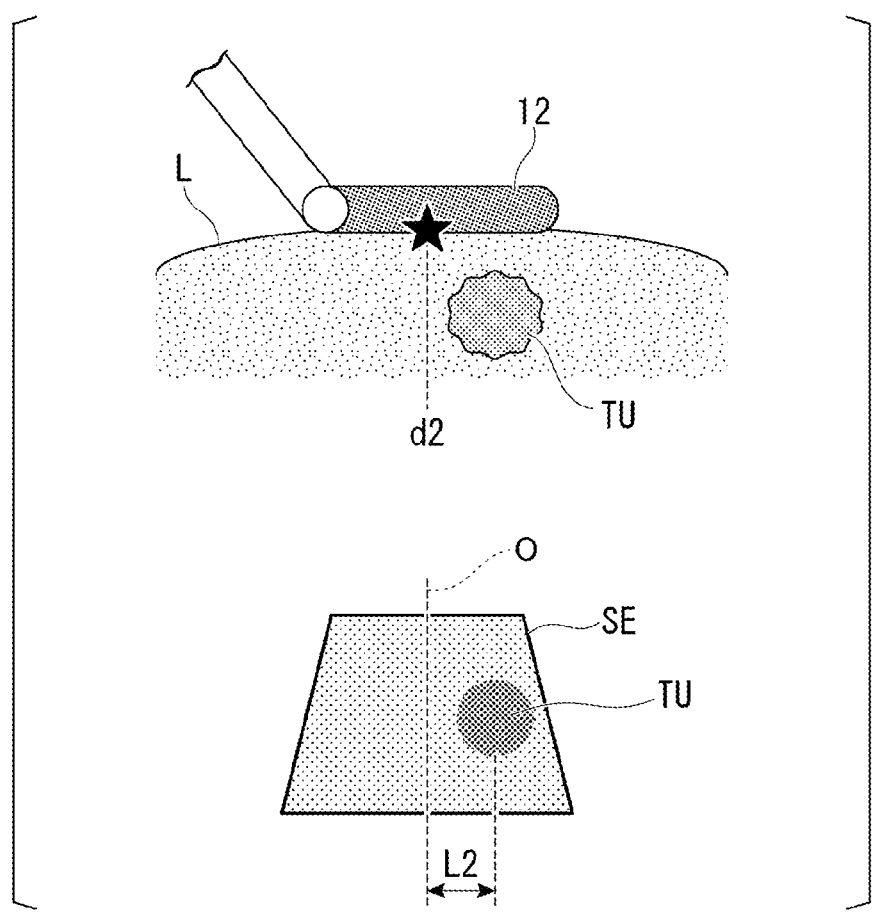
FIG. 15 is a diagram showing an example of the relationship between the first reference position and the first echo image.

FIG. 14 is a diagram showing a display image D1 in which the first reference position image S is superimposed and displayed. FIG. 15 is a diagram showing an example of the relationship between the first reference position P and the first echo image SE. In the second embodiment, the target tissue TU may not be reflected on the central axis O in the first echo image SE. Next, the control device 3 executes step S32.

In step S32, the control device 3 estimates the position of the target tissue TU (second reference position estimation step). For example, the control device 3 assumes that the observation direction d1 of the treatment portion 12 of the ultrasonic probe 1 coincides with the normal direction d2 of the surface of the liver L at the first reference position P, to estimate the position of the target tissue TU (second reference position Q). Next, the control device 3 executes step S33.

Figure 16:
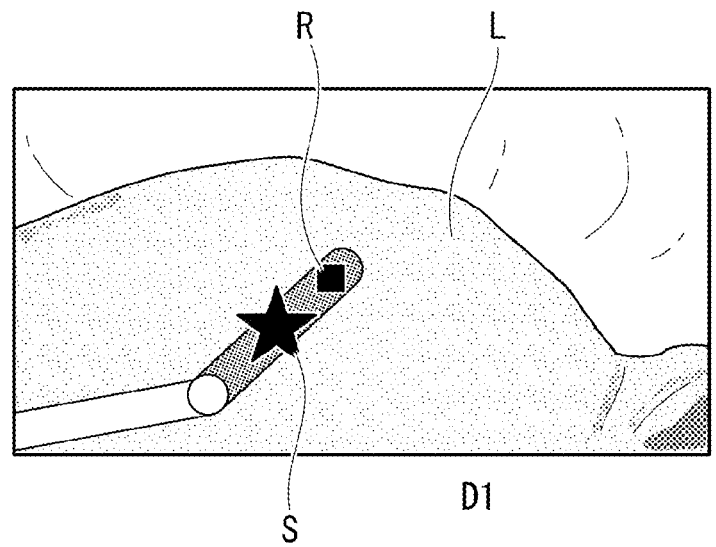
FIG. 16 is a diagram showing a display image in which a second reference position image is superimposed and displayed.

FIG. 16 is a diagram showing a display image D1 on which the second reference position image R is superimposed and displayed.

In step S33, the control device 3 superimposes and displays the second reference position image R on the estimated position of the target tissue TU (second reference position Q) with respect to the display image D1 (second reference position image display step). In the present embodiment, the second reference position image R is a rectangular image, but the second reference position image R is not limited to this.

Figure 17:
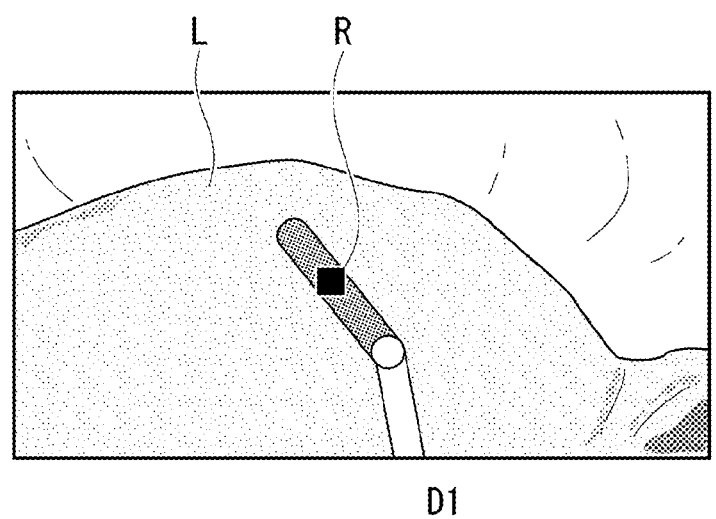
FIG. 17 is a diagram showing a display image when the position of the treatment portion is changed.

FIG. 17 is a diagram showing a display image D1 when the position of the treatment portion 12 is changed. The surgeon rotates the treatment portion 12 of the ultrasonic probe 1 around the second reference position image R displayed on the display image D1. The surgeon rotates the treatment portion 12 so that the center of the treatment portion 12 in the longitudinal axis direction (first reference position image S) coincides with the target tissue position image R. The surgeon rotates the treatment portion 12 while generally maintaining the state in which the treatment portion 12 is arranged on the tangent plane between the treatment portion 12 and the surface of the liver L. The tangent plane is a plane perpendicular to the normal direction d2 of the surface of the liver L. In the example shown in FIG. 17, the treatment portion 12 of the ultrasonic probe 1 is rotated by about 90 degrees about the first reference position image S, but the rotation angle is not limited to this.

Next, the control device 3 executes step S15. Steps S15 to S17 are the same as in the first embodiment. The control device 3 records the second echo image AE and detects the difference in the position of the target tissue TU with respect to the central axis O in the second echo image AE. Next, the control device 3 executes step S34.

In step S34, the control device 3 compares the difference in position detected in step S17 with a predetermined threshold value. In a case where the difference in the position of the target tissue TU with respect to the central axis O is smaller than a predetermined threshold value, it can be determined that the target tissue TU is located in the normal direction d2 of the surface of the liver L at the second reference position Q. On the other hand, in a case where the difference in the position of the target tissue TU with respect to the central axis O is equal to or larger than a predetermined threshold value, or in a case where the target tissue TU is not displayed on the second echo image AE, it can be determined that there is no target tissue TU in the normal direction d2 of the surface of the liver L at the second reference position Q. In a case where the difference between the positions detected in step S17 is equal to or greater than a predetermined threshold value, the control device 3 executes step S19. In a case where the difference between the positions detected in step S17 is smaller than the predetermined threshold value, the control device 3 executes step S20.

According to the medical system 100B of the present embodiment, it is possible to detect the difference in the position of the target tissue TU with respect to the central axis O of the second echo image AE. Even in a case where the target tissue TU is not shown in the center of the first echo image SE, it is possible to support the determination of whether or not the target tissue TU is present in the normal direction d2 of the surface of the liver L at the second reference position Q. Therefore, it is possible to streamline the work for estimating the accurate position of the target tissue TU in the liver L.

Although the second embodiment of the present invention has been described in detail with reference to the drawings, the specific configuration is not limited to this embodiment and includes design changes and the like within a range not deviating from the gist of the present invention. In addition, the components shown in the above-described embodiments and modifications can be appropriately combined and configured.

Third Embodiment

The third embodiment of the present invention will be described with reference to FIGS. 18 to 20. In the following description, the same reference numerals will be given to the configurations common to those already described, and duplicate description will be omitted.

A medical system 100C includes an ultrasonic probe 1, an endoscope 2, a control device 3, a display device 4, and an input device 5, as in the medical system 100 according to the first embodiment. The medical system 100C differs from the medical system 100 according to the first embodiment only in the control performed by a treatment portion 12 and the control device 3. Hereinafter, a description will be given according to the control flowchart of the control device 3 shown in FIG. 18.

Unlike the first embodiment and the second embodiment, the treatment portion 12 performs only linear scanning. In this case, the cross section scanned by the treatment portion 12 is a cross section parallel to the longitudinal axis of the treatment portion 12 and is rectangular.

As in the first embodiment, the surgeon operates the ultrasonic probe 1 so that the target tissue TU of the liver L to be treated is displayed on the echo image D2 displayed on the display device 4 while observing the display image D1. In the third embodiment, as in the second embodiment, the target tissue TU may not be displayed on the central axis O of the echo image D2.

Figure 18:
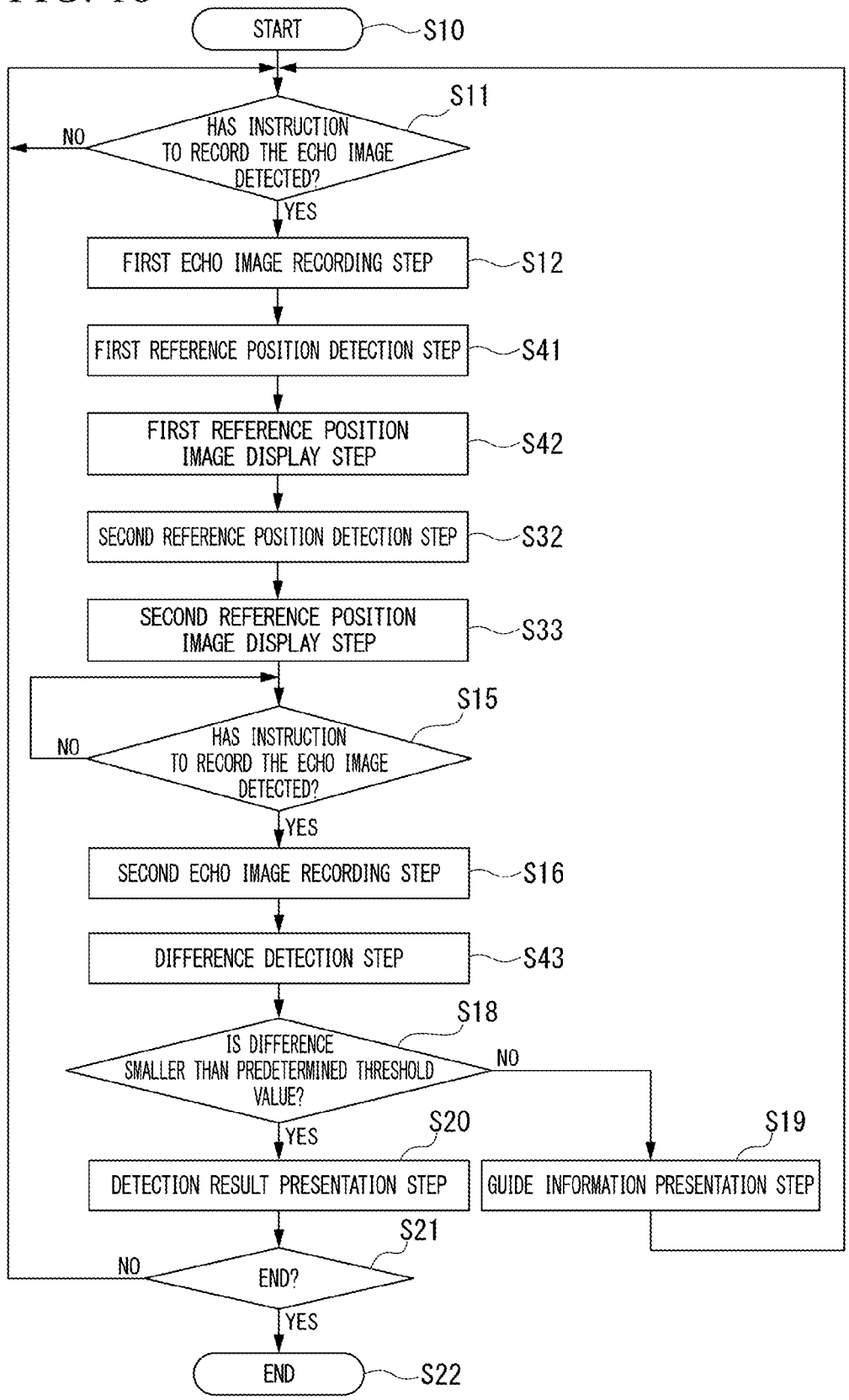
FIG. 18 is a control flowchart of a medical system according to a third embodiment of the present invention.

As shown in FIG. 18, when the control device 3 is activated, the control device 3 starts control after performing initialization (step S10). Next, the control device 3 executes step S11. Steps S11 to S12 are the same as those in the first embodiment. The control device 3 records the first echo image SE. Next, the control device 3 executes step S41.

Figure 19:
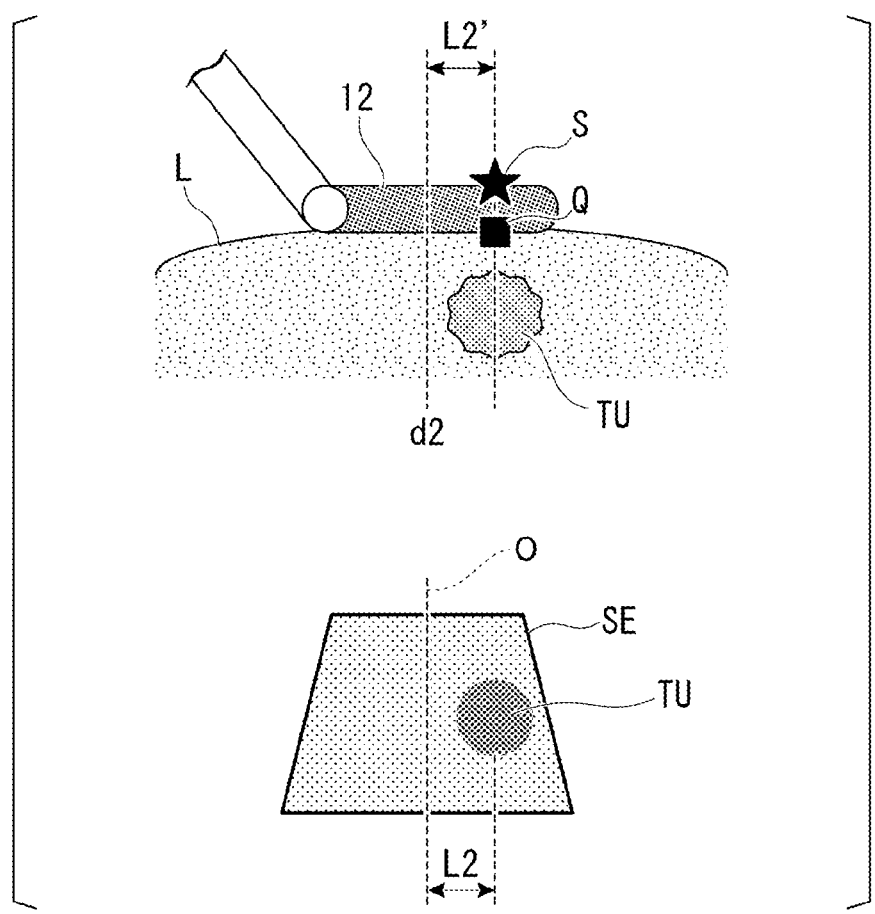
FIG. 19 is a diagram showing an example of the relationship between the first reference position and the first echo image.

FIG. 19 is a diagram showing an example of the relationship between the first reference position P and the first echo image SE.

In step S41, the control device 3 detects the first reference position P, which is the position corresponding to the target tissue TU on the treatment portion 12 of the ultrasonic probe 1 when the first echo image SE is recorded (first reference position detection step). Specifically, first, in the first echo image SE recorded in step S12, the difference L2 of the position of the target tissue TU with respect to the central axis O is detected. Then, the difference L2' in the display image D1 is calculated based on the difference L2 in the first echo image SE. Then, in the treatment portion 12 in the display image D1, a position deviated from the center position in the longitudinal axis direction of the treatment portion 12 by a distance L2' is detected as the first reference position P.

Next, the control device 3 executes step S42. In step S42, the control device 3 superimposes and displays the first reference position image S on the first reference position P detected in step S41. Then, when the treatment portion 12 is moved in the display image D1, the first reference position image S is also followed and displayed. Specifically, the first reference position image S is always displayed at the first reference position P of the treatment portion 12 in accordance with the movement of the treatment portion 12. In the present embodiment, the first reference position image S is a star-shaped image, but the first reference position image S is not limited to this.

Next, the control device 3 executes step S31. Steps S31 to S32 are the same as in the second embodiment.

Next, the surgeon rotates the treatment portion 12 of the ultrasonic probe 1 around the second reference position image R displayed on the display image D1. The surgeon rotates the treatment portion 12 by matching the first reference position image S of the treatment portion 12 with the target tissue position image R. The surgeon rotates the treatment portion 12 while generally maintaining the state in which the treatment portion 12 is arranged on the tangent plane between the treatment portion 12 and the surface of the liver L. The tangent plane is a plane perpendicular to the normal direction d2 of the surface of the liver L.

Next, the control device 3 executes step S15. Steps S15 to S16 are the same as in the first embodiment. Next, the control device 3 executes step S43.

Figure 20:
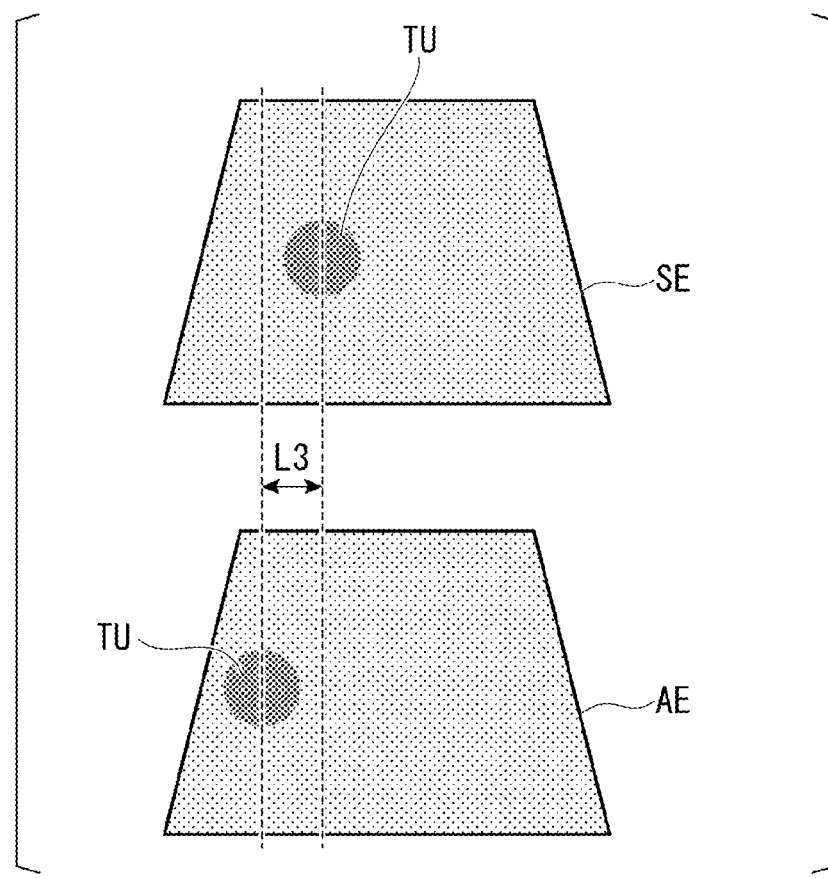
FIG. 20 is a diagram showing an example of the relationship between the first echo image and the second echo image.

FIG. 20 is a diagram showing an example of the relationship between the first echo image SE and the second echo image AE.

In step S43, the control device 3 compares the position of the target tissue TU in the first echo image SE with the position of the target tissue TU in the second echo image AE, and detects the difference (positional deviation) in the position of the target tissue TU (difference detection step). For example, as shown in FIG. 20, the position of the target tissue TU in the first echo image SE and the position of the target tissue TU in the second echo image AE are located at positions separated by L3 in the horizontal direction perpendicular to the central axis O, and the difference in position is L3.

Next, the control device 3 executes step S18. Step S18 is the same as the first embodiment. Further, the subsequent steps S19 to S22 are the same as those in the first embodiment.

According to the medical system 100C of the present embodiment, it is possible to detect the difference between the position of the target tissue TU in the first echo image SE and the position of the target tissue TU in the second echo image AE. Even in a case where the treatment portion 12 is of the linear method and the target tissue TU is not shown in the center of the first echo image SE, it is possible to support the determination of whether or not the target tissue TU is present in the normal direction d2 of the surface of the liver L at the second reference position Q. Therefore, it is possible to streamline the work for estimating the accurate position of the target tissue TU in the liver L.

Although the third embodiment of the present invention has been described in detail with reference to the drawings, the specific configuration is not limited to this embodiment and includes design changes and the like within a range not deviating from the gist of the present invention. In addition, the components shown in the above-described embodiments and modifications can be appropriately combined and configured.

The present invention can be applied to a medical system using an ultrasonic probe.

What is claimed is:

1. A control apparatus for use in a medical system, the control apparatus comprising:
   a processor comprising hardware, the processor being configured to:
      acquire a first echo image from a first ultrasonic wave acquired by an ultrasonic probe in which a target tissue is displayed on a central axis,
      acquire a second echo image from a second ultrasonic wave acquired by the ultrasonic probe obtained by scanning a cross section different from the first echo image at a reference position of the ultrasonic probe from which the first echo image was acquired, and
      compare a central axis of the second echo image with a position of the target tissue in the second echo image;
   wherein the processor is configured to detect a difference in the position of the target tissue in the second echo image with respect to the central axis of the second echo image.

2. The control apparatus according to claim 1, wherein the processor is configured to compare the difference with a predetermined threshold value.

3. The control apparatus according to claim 2, wherein, in a case where the difference is equal to or greater than the predetermined threshold value, the processor is configured to:
  generate a display image from a captured image acquired by an endoscope, and
  display a guide image on the display image based on the difference.

4. The control apparatus according to claim 1, wherein the processor is configured to:
  generate a display image from a captured image acquired by an endoscope, and
  calculate the reference position in the display image based on a display image obtained from the first echo image.

5. The control apparatus according to claim 1, wherein the processor is configured to:
  receive an instruction input to the ultrasonic probe;
  acquire the first echo image based on the instruction, and
  acquire the second echo image based on the instruction.

6. A control apparatus for use in a medical system, the control apparatus comprising:
  a processor comprising hardware, the processor being configured to:
    acquire a first echo image from a first ultrasonic wave acquired by an ultrasonic probe in which a target tissue is displayed,
    calculate a reference position based on a position of the target tissue in the first echo image,
    acquire a second echo image from a second ultrasonic wave acquired by the ultrasonic probe obtained by scanning a cross section different from the first echo image at the reference position, and
    compare a central axis of the second echo image with a position of the target tissue in the second echo image;
  wherein the processor is configured to detect a difference in the position of the target tissue in the second echo image with respect to the central axis of the second echo image.

7. A control apparatus for use in a medical system, the control apparatus comprising:
  a processor comprising hardware, the processor being configured to:
    acquire a first echo image from a first ultrasonic wave acquired by an ultrasonic probe in which a target tissue is displayed,
    acquire a second echo image from a second ultrasonic wave acquired by the ultrasonic probe obtained by scanning a cross section different from the first echo image, and
    compare a position of the target tissue in the first echo image with a position of the target tissue in the second echo image;
  wherein the processor is configured to detect a difference in the position of the target tissue in the second echo image with respect to the position of the target tissue in the first echo image.

8. The control apparatus according to claim 7, wherein the processor is configured to:
  calculate a reference position based on the position of the target tissue in the first echo image, and
  acquire the second echo image obtained by scanning a cross section different from the first echo image at the reference position.

9. A control method comprising:
  acquiring a first echo image from a first ultrasonic wave acquired by an ultrasonic probe in which a target tissue is displayed on a central axis,
  acquiring a second echo image from a second ultrasonic wave acquired by the ultrasonic probe obtained by scanning a cross section different from the first echo image at a reference position of the ultrasonic probe from which the first echo image was acquired, and
  comparing a central axis of the second echo image with a position of the target tissue in the second echo image; and
  detecting a difference in the position of the target tissue in the second echo image with respect to the position of the target tissue in the first echo image.

10. A medical system comprising:
  the control apparatus according to claim 1;
  an endoscope; and
  the ultrasonic probe.

11. The control apparatus according to claim 1, wherein the processor is configured to:
  generate a display image from a captured image acquired by an endoscope, and
  superimpose a reference position image on the reference position with respect to the display image.

12. The control apparatus according to claim 1, wherein the reference position is a center of a treatment portion of the ultrasonic probe.

13. A medical system comprising:
  the control apparatus according to claim 6;
  an endoscope; and
  an ultrasonic probe.

14. The control apparatus according to claim 6, wherein the processor is configured to:
  generate a display image from a captured image acquired by an endoscope, and
  superimpose a reference position image on the reference position with respect to the display image.

15. A medical system comprising:
  the control apparatus according to claim 7;
  an endoscope; and
  an ultrasonic probe.

16. The control apparatus according to claim 8, wherein the processor is configured to:
  generate a display image from a captured image acquired by an endoscope, and
  superimpose a reference position image on the reference position with respect to the display image.

17. The control method according to claim 9, further comprising detecting a difference in the position of the target tissue in the second echo image with respect to the central axis of the second echo image.

* * * * *